(12) United States Patent
Park et al.

(10) Patent No.: US 11,918,781 B2
(45) Date of Patent: Mar. 5, 2024

(54) INFUSION FLOW REGULATOR

(71) Applicant: KOREA AEROSPACE RESEARCH INSTITUTE, Daejeon (KR)

(72) Inventors: Poo Min Park, Daejeon (KR); Hyung Mo Kim, Daejeon (KR); Tae Choon Park, Daejeon (KR); Young Seok Kang, Daejeon (KR); Jae Sung Huh, Daejeon (KR); Doo Yong Lee, Daejeon (KR)

(73) Assignee: Korea Aerospace Research Institute, Daejeon (KR)

( * ) Notice: Subject to any disclaimer, the term of this patent is extended or adjusted under 35 U.S.C. 154(b) by 426 days.

(21) Appl. No.: 17/254,994

(22) PCT Filed: May 27, 2019

(86) PCT No.: PCT/KR2019/006317
§ 371 (c)(1),
(2) Date: Dec. 22, 2020

(87) PCT Pub. No.: WO2019/245178
PCT Pub. Date: Dec. 26, 2019

(65) Prior Publication Data
US 2021/0260281 A1    Aug. 26, 2021

(30) Foreign Application Priority Data
Jun. 22, 2018   (KR) .......................... 10-2018-0071924

(51) Int. Cl.
*A61M 5/168* (2006.01)

(52) U.S. Cl.
CPC .... *A61M 5/16877* (2013.01); *A61M 5/16804* (2013.01); *A61M 5/16813* (2013.01)

(58) Field of Classification Search
CPC ...... A61M 2205/33; A61M 2205/3334; A61M 5/168; A61M 5/16804; A61M 5/16813; A61M 5/16877; A61M 5/16881; A61M 39/22; A61M 2039/229; A61M 2005/3331; A61M 2005/3379
See application file for complete search history.

(56) References Cited

FOREIGN PATENT DOCUMENTS

KR    101487754 B1 *  1/2015    ............. A61M 5/36
KR    101487754 B1    1/2015

* cited by examiner

*Primary Examiner* — Shefali D Patel
(74) *Attorney, Agent, or Firm* — Rabin & Berdo, P.C.

(57) ABSTRACT

An infusion flow regulator includes: a main body having an inlet through which fluid is introduced and an outlet through which the fluid is discharged; and a rotary dial rotatably coupled to the main body, with a sealing member interposed therebetween, so as to regulate a flow rate of the fluid, in which the rotary dial includes a regulating flow path having a shape of a recessed groove in cross section with a first width and a first height, and the regulating flow path includes a first region in which the first width is constant and the first height is decreased, and a second region in which both the first width and the first height are decreased. By the aforementioned configuration, the infusion flow regulator for the fluid can accurately regulate the flow rate even in a region where the flow rate of the fluid is very small.

12 Claims, 8 Drawing Sheets

INFUSION FLOW REGULATOR

CROSS-REFERENCE TO RELATED APPLICATIONS

This patent application is a U.S. national stage application of International Application No. PCT/KR2019/006317, filed May 27, 2019 and the entire contents of which are incorporated herein by reference, which claims priority to KR 10-2018-0071924, filed Jun. 22, 2018 and the entire contents of which are incorporated herein by reference.

TECHNICAL FIELD

The present disclosure relates to an infusion flow regulator used for regulating a flow rate of an infusion solution to be administered for infusion therapy, and, to an infusion flow regulator including an arc-shaped flow path for regulating a distance by which the infusion solution is passed through, and a circular flow path for inducing a discharge of the infusion solution that has passed through the arc-shaped flow path, and capable of finely regulating the flow rate with the flow path that has an improved in cross section.

BACKGROUND

The infusion set is a medical device to administer infusion solution contained in an infusion solution bottle to a patient at a target flow rate that is regulated according to the prescription, and it includes a tube-shaped flow path with one end connected to the infusion solution bottle and the other end equipped with an injection needle, to inject the infusion solution into the human body, and the tube flow path of the infusion flow regulator has a roller clamp that regulates the flow rate of the infusion solution by changing the cross-sectional area of the flow path of the tube by a vertical movement of a roller.

Recently, many tools are developed for the infusion flow regulator to precisely regulate the flow rate of the infusion solution, and Korean Registered Patent No. 10-1487754 discloses a flow rate regulating principle as an example of the related infusion flow regulator.

Figure 1:
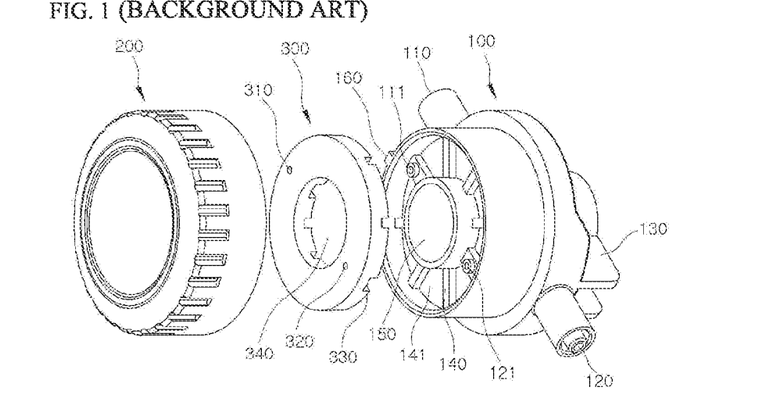
FIGS. 1 to 3 show examples of an infusion flow regulator according to the related art.
Figure 2:
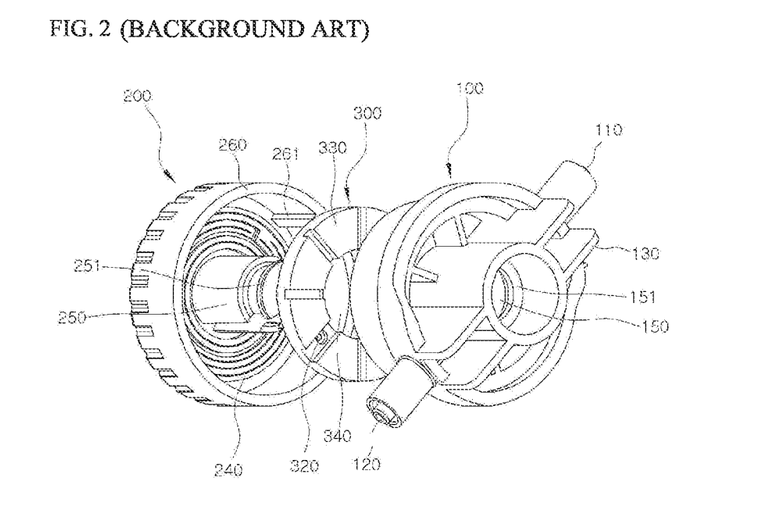
Figure 3:
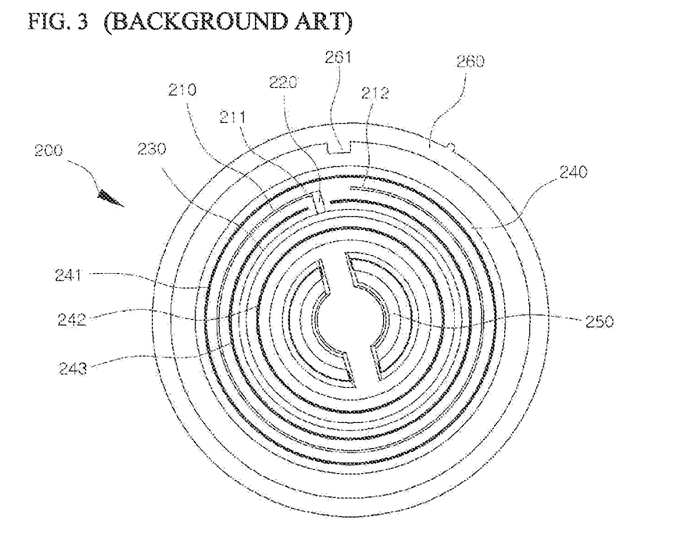

Referring to FIGS. 1 to 3 of the drawings of Korean Registered Patent No. 10-1487754, the related art will be schematically described below. The infusion flow regulator includes a second body 100 having an inlet port 110 and an outlet port 120 configured to have both cut tubes of an infusion solution set fastened and connected thereto so that an infusion solution is introduced through the inlet port 110, a flow rate of the infusion solution is regulated by a first body 200, and then the infusion solution is discharged through the outlet port 120, the first body 200 rotatably mounted on the second body 100 and having a flow path arranged between the inlet port 110 and the outlet port 120 to enable a flow rate to be regulated by a flow path configured to change a flow resistance by having a rotation angle changed, and a sealing member 300 interposed between the second body 100 and the first body 200 to seal the flow path of the first body 200.

The first body 200 includes an insertion piece 250 formed to protrude from a center of a rear surface and to be inserted into a fastening hole 150 of the second body 100 to serve as a rotating axis, a flow path forming surface 240 formed as a single flat surface near the insertion piece 250 of the rear surface and closely adhered to a sealing member seating surface 140 of the second body 100 while the sealing member 300 is interposed between the first body 200 and the second body 100 when the first body 200 is mounted on the second body 100, an arc-shaped flow path 210, a connecting flow path 220, and a circular flow path 230 formed on the flow path forming surface 240, an outer circumferential surface part 260 formed to surround an outer circumferential surface of a portion made to protrude to form the sealing member seating surface 140 of the second body 100 when mounted on the second body 100 at a predetermined interval, a hooking protrusion 261 formed to protrude from an inner circumferential surface of an outer circumferential surface part 260 to be hooked and stopped by a stopper 160 at a predetermined rotation angle when the first body 200 is rotated, and gradations 270 which are formed along a circumferential direction of the outer circumferential surface part 260.

The circular flow path 230 is formed to be a recessed groove and formed so as to be a circular shape around the insertion piece 250, thereby forming a circular closed curve. The arc-shaped flow path 210 is also formed to be a recessed groove and formed so as to be an arc shape having a radius larger than that of the circular flow path 230 around the rotating axis. Thus, a closed curve is not formed. The positions of forming the hooking protrusion 261 and the stopper 160 of the second body 100 are aligned so that the hooking protrusion 261 and the stopper 160 stop rotation of the first body 200 at a point deviating from the central angle of the arc-shaped flow path 210 (i.e., a point deviating from the arc-shaped flow path 210) after being aligned to the other end 212 of the arc-shaped flow path 210.

In this way, one end 211 of the arc-shaped flow path 210 which is concentric with the circular flow path 230 is connected to the circular flow path 230 by the connecting flow path 220 formed to extend in the shape of a recessed groove toward the circular flow path 230. The other end 212 of the arc-shaped flow path 210 remains blocked. Accordingly, a flow path is formed, which forms an arc starting from the other end 212 of the arc-shaped flow path 210 and then connected to the circular flow path 230 by the connecting flow path 220 at the one end 211.

The arc-shaped flow path 210, the connecting flow path 220, and the circular flow path 230 formed as described above form a flow path which is covered and sealed by the sealing member 300. The cross-sectional shapes of the arc-shaped flow path 210, the connecting flow path 220, and the circular flow path 230 will be described below.

The arc-shaped flow path 210 has a uniform width throughout an entire section, but then as a depth thereof gradually deepens from the other end 212, which is blocked, to the one end 211 which is connected to the connecting flow path 220, a cross-sectional area is gradually increased from the other end 212 to the one end 211. Because a width and a depth of the circular flow path 230 are uniform throughout an entire section, a cross-sectional area thereof is also uniform throughout the entire section.

The flow path of the flow of the infusion solution introduced into the infusion flow regulator will be described. Once introduced, the infusion solution is introduced into the arc-shaped flow path 210, passed through the arc-shaped flow path, passed through the circular flow path 230 through the connecting flow path 220, and then discharged to the outside of the infusion flow regulator, in which the flow rate is regulated by changing the length by which the solution is passed through the arc-shaped flow path 210, and the variations in the length of the arc-shaped flow path is regulated by rotating the first body 200.

However, in the related art, the arc-shaped flow path 210, which is a part for regulating the flow rate, has a form in which the width is uniform and the depth (hereinafter referred to as 'height' for convenience of explanation) is changed throughout the entire section, as conceptually illustrated in FIG. 4.

Figure 4:
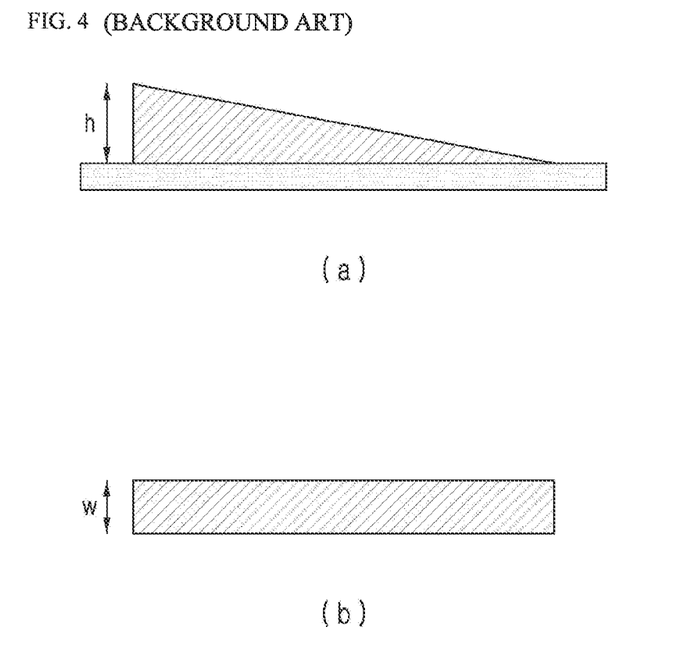
FIG. 4 shows a height and a width of an arc-shaped flow path in arc shape of the infusion flow regulator according to the related art.

FIG. 4 conceptually shows the arc of the arc-shaped flow path 210 having a recessed groove shape of the infusion flow regulator according to the related art, which is straightened out to a linear form for convenience of description, in which FIG. 4A shows a side cross-sectional view showing the height change according to the length of the arc-shaped flow path 210, and FIG. 4B shows the constant width when the arc-shaped flow path 210 is viewed from above. As apparent from the drawings, the height of the arc-shaped flow path decreases linearly with the length, but the width remains constant.

However, the related technology has the following problems.

The arc-shaped flow path 210 forms a flow path that is covered and sealed with the sealing member 300, in which the sealing member is generally formed of a soft material and thus pressed slightly into the open surface of the flow path, resulting in a reduction in the cross-sectional area of the flow path, and the reduction in the cross-sectional area of the flow path gives a relatively greater influence at the end of the flow path (the portion through which micro flow rate is passed), and in severe cases, the flow path is blocked, making it difficult to accurately regulate the micro flow rate. In the related infusion flow regulator, when regulating a very small amount of infusion solution at a microscopic level of regulating range, there is a problem that the infusion solution does not flow out even when the regulator is opened.

The infusion flow regulator used for infusion therapy is a device that has a flow path with a width of about 0.15 mm therein to regulate a relatively low flow rate of several to several hundred ml per hour, and it is necessary to accurately supply a very low flow rate of several ml/h in the case of chemotherapy or children, but it is difficult to regulate such a very small flow rate with the related technology.

SUMMARY

Technical Problem

The present disclosure has been made to overcome the problems mentioned above, and it is an object of the present disclosure to provide an infusion flow regulator capable of regulating even a very small flow rate of an infusion solution by improving variations in width and height of an arc-shaped flow path in the infusion flow regulator.

Technical Solution

The present disclosure provides an infusion flow regulator, including: a main body 10 having an inlet through which fluid is introduced and an outlet through which the fluid is discharged; and a rotary dial 30 rotatably coupled to the main body, with a sealing member 20 interposed therebetween, so as to regulate the flow rate of the fluid, in which the rotary dial includes a regulating flow path 31 having a shape of a recessed groove in cross section with a first width and a first height, and the regulating flow path 31 includes a first region in which the width is constant and the height is decreased, and a second region in which both the width and height are decreased.

The infusion flow regulator further includes a collector flow path 33 having a shape of a recessed groove in cross section and in communication with the regulating flow path to guide the fluid, and it is preferable that the width and height of the collector flow path are constant.

The regulating flow path is an arc-shaped flow path, and the collector flow path is a circular flow path, in which the infusion flow regulator further includes a connecting flow path connecting the regulating flow path and the collector flow path.

The height of the regulating flow path is linearly decreased in the first region, and the second region may be formed over a region ⅓ to ½ of a length of the regulating flow path.

The second region may begin at a point where the height, which is decreasing in the first region, becomes equal to the width.

The cross-section of the regulating flow path may have a rectangular shape in the first region, and the cross-section of the regulating flow path may have a square shape in the second region.

Advantageous Effects

The infusion flow regulator according to the present disclosure has an effect of accurately regulating the flow rate even in a region where the flow rate of the infusion solution is a very small by the configuration described above.

DETAILED DESCRIPTION

The objectives, specific advantages and novel features of the present invention will become more apparent from the following detailed description and the preferred embodiments, which are associated with the accompanying drawings. In addition, terms described herein are terms defined in consideration of functions in the present invention, which may vary according to the intention or convention of a user or an operator. Therefore, definitions of these terms should be made based on the contents throughout the present specification.

The present disclosure developed an infusion flow regulator that accurately regulates a micro flow rate, which is required for chemotherapy or children where it is required to accurately supply a very low flow rate of several ml/h. The inventors have found that, in the related regulator, the sealing member (flexible seal) used for regulating the flow rate is expanded into the flow path in recessed groove shape, and the decrease in the flow path area by this expansion is due to the relatively large influence at low flow rates with low flow path height, and also found that, when the flow path height is low, the aspect ratio of the width and height of the flow path increases, and the hydrodynamic hydraulic area is severely reduced, and in the region where the height of the flow path is low, the hydraulic area decreases more severely than the actual area is decreased such that the flow rate does not increase linearly, and have arrived at the present disclosure based on these findings. Hereinafter, the present disclosure will be described in detail with reference to the accompanying drawings.

Figure 5:
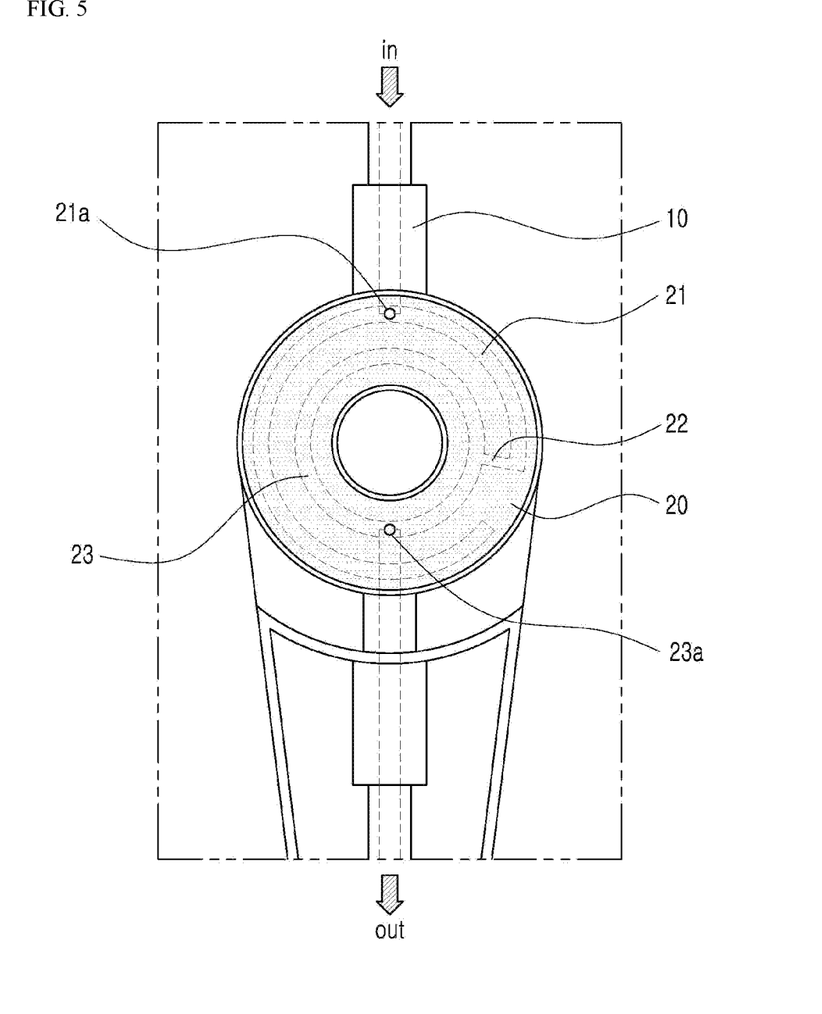
FIG. 5 shows a sealing member coupled to a main body of an infusion flow regulator according to an embodiment of the present disclosure.
Figure 6:
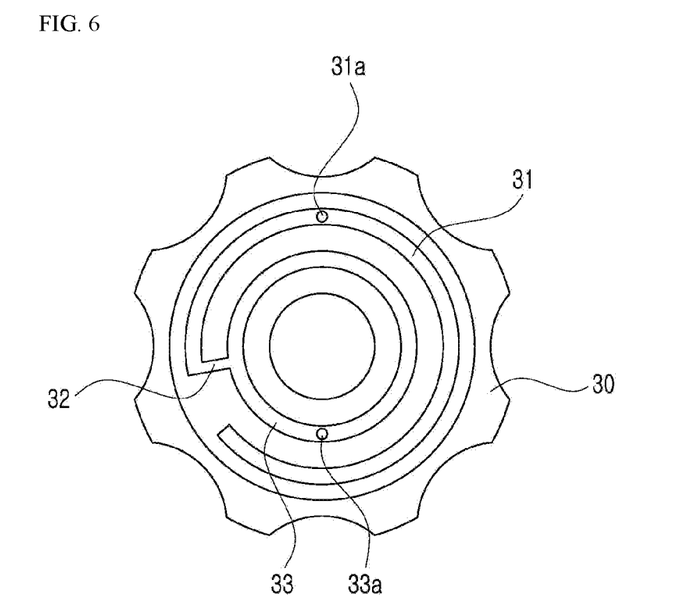
FIG. 6 shows a rotary dial of the infusion flow regulator according to an embodiment of the present disclosure.
Figure 7:
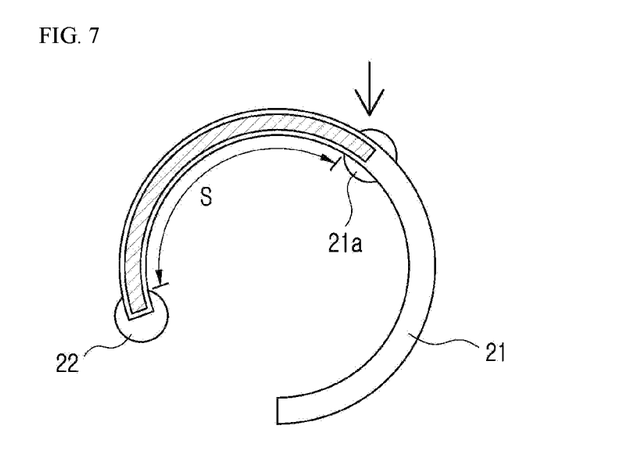
FIG. 7 is a conceptual view showing a regulating flow path of the infusion flow regulator according to an embodiment of the present disclosure.
Figure 8:
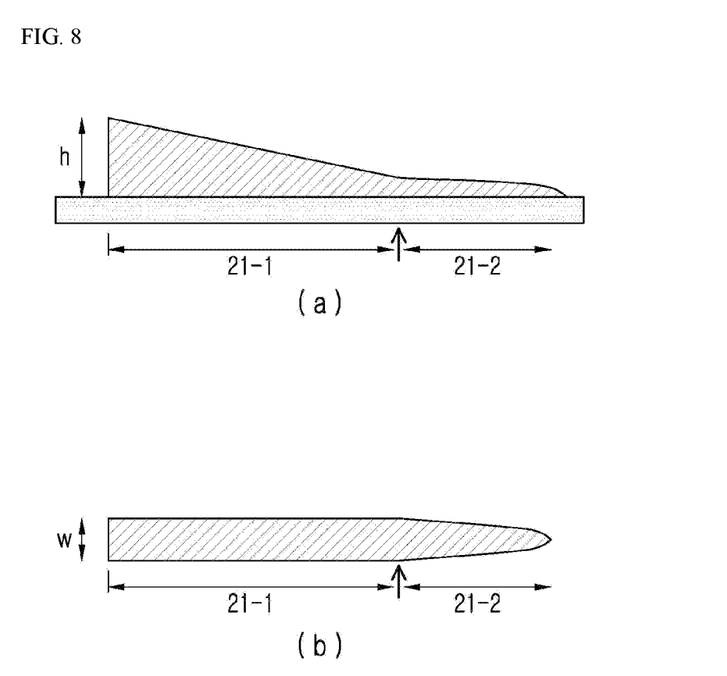
FIG. 8 shows a height and a width of a regulating flow path of the infusion flow regulator according to an embodiment of the present disclosure.
Figure 9:
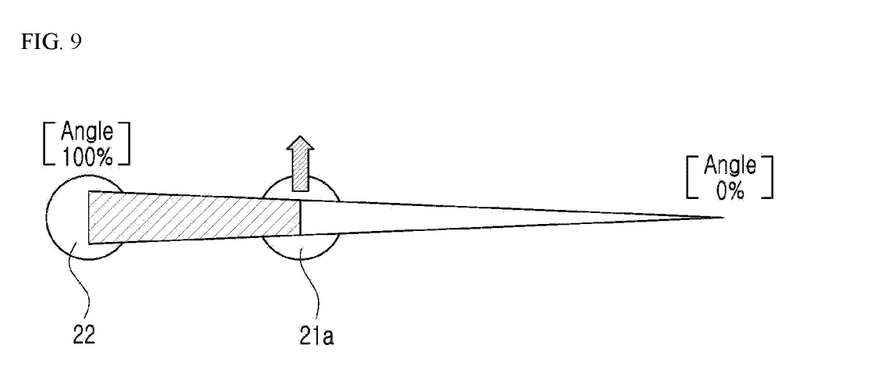
FIG. 9 is a conceptual view showing a flow of infusion solution flowing through the regulating flow path in the infusion flow regulator according to an embodiment of the present disclosure.
Figure 10:
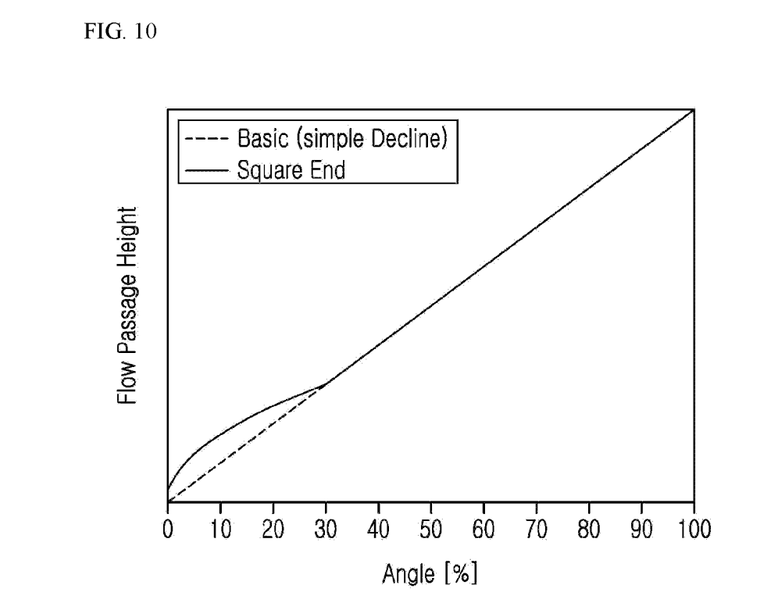
FIGS. 10 and 11 are graphs showing, by comparison, variations in height and width of the related infusion flow regulator and the infusion flow regulator according to the present disclosure.
Figure 11:
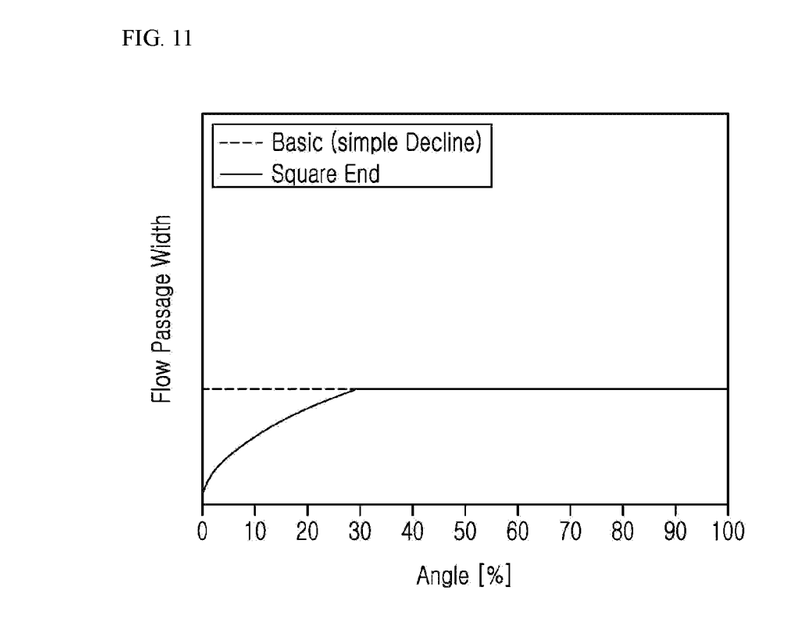
Figure 12:
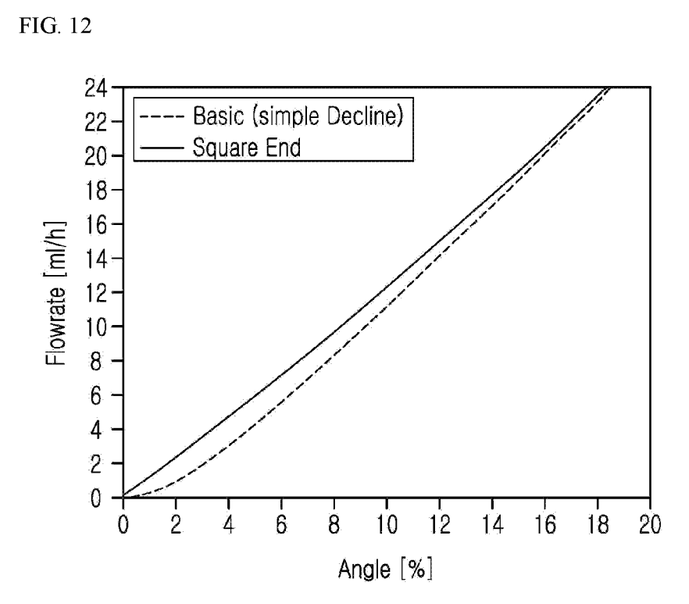
FIG. 12 is a graph showing, by comparison, the flowing state of the flow rate of the related infusion flow regulator and the infusion flow regulator according to the present disclosure.
Figure 13:
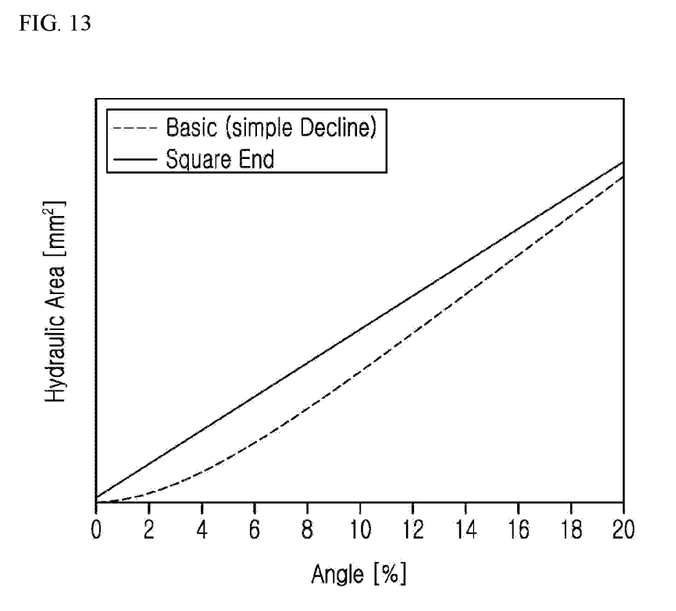
FIG. 13 is a graph showing, by comparison, a hydraulic area in the microscopic flow rate range of the related infusion flow regulator and the infusion flow regulator according to the present disclosure.
Figure 14:
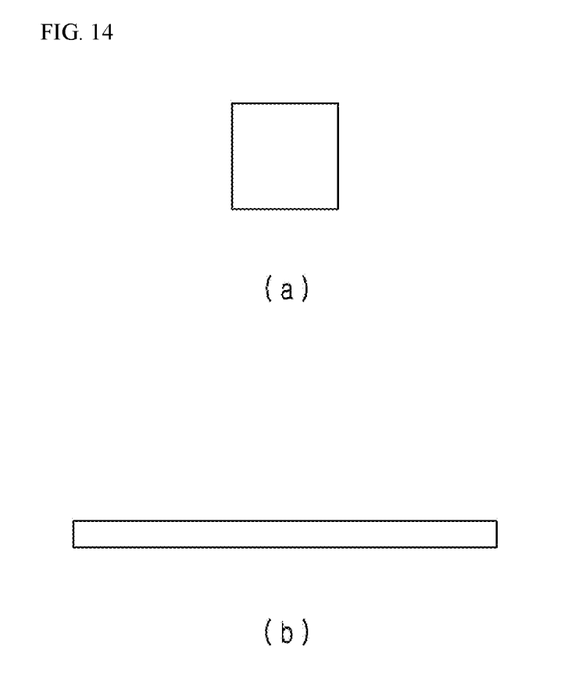
FIG. 14 is a view showing, by comparison, a cross-sectional shape of a regulating flow path in a micro flow rate range between the related infusion flow regulator and the infusion flow regulator according to the present disclosure.

FIG. 5 shows a sealing member coupled to a main body of an infusion flow regulator according to an embodiment of the present disclosure, FIG. 6 shows a rotary dial of the infusion flow regulator according to an embodiment of the present disclosure, FIG. 7 is a conceptual view showing a regulating flow path of the infusion flow regulator according to an embodiment of the present disclosure, FIG. 8 shows a height and a width of a regulating flow path of the infusion flow regulator according to an embodiment of the present disclosure, FIG. 9 is a conceptual view showing a flow of infusion solution flowing through the regulating flow path in the infusion flow regulator according to an embodiment of the present disclosure, FIGS. 10 and 11 are graphs showing, by comparison, variations in height and width of the related infusion flow regulator and the infusion flow regulator according to the present disclosure, FIG. 12 is a graph showing, by comparison, the flowing state of the flow rate of the related infusion flow regulator and the infusion flow regulator according to the present disclosure, FIG. 13 is a graph showing, by comparison, a hydraulic area in the microscopic flow rate range of the related infusion flow regulator and the infusion flow regulator according to the present disclosure, and FIG. 14 is a view showing, by comparison, a cross-sectional shape of a regulating flow path in a micro flow rate range between the related infusion flow regulator and the infusion flow regulator according to the present disclosure.

First, the present disclosure is directed to an infusion flow regulator for quantitatively injecting infusion solution into a patient, and except for the characteristic in which the cross-sectional area of the flow path is changed to a new shape to regulate the flow rate of fluid (infusion solution) being injected, it has the similar shape to that of the related infusion flow regulator, and accordingly, the overall shape of the infusion flow regulator is similar to that of the related regulator in certain ways. Accordingly, description of the general shape of the infusion flow regulator will be omitted, and the core characteristics of the present disclosure will be mainly described.

FIG. 5 shows a sealing member 20 coupled to a main body 10 as a component of the infusion flow regulator according to an embodiment of the present disclosure, and FIG. 6 shows a rotary dial 30. The infusion flow regulator of the present disclosure has a structure in which the rotary dial 30 is coupled to the main body 10, and the infusion solution is introduced through an inlet (in) at an upper side of the main body and discharged to a lower outlet (out) of the main body. In addition, as the rotary dial is rotated, the degree of flow of the infusion solution is regulated.

Referring to FIG. 6, the rotary dial 30 includes a regulating flow path 31, a connecting flow path 32, and a collector flow path 33, each of which is formed in a recessed groove shape. The regulating flow path 31 does not completely form a circle at an outer edge of the collector flow path 33, but forms an arc-shaped shape. In addition, the collector flow path 33 has a shape that completely forms a circle. In addition, the connecting flow path 32 is a flow path connecting the regulating flow path and the collector flow path to each other.

In FIG. 5, although reference numerals 21, 22, and 23 indicated by dotted lines are not described, these indicate the positions corresponding to the regulating flow path 31, the connecting flow path 32, and the collector flow path 33 respectively when the rotary dial 30 is coupled. In addition, the sealing member 20 of FIG. 5 includes a regulating flow path inlet 21a through which the infusion solution is injected into the regulating flow path 21, and a collector flow path outlet 23a through which the infusion solution of the collector flow path 23 is discharged. That is, the infusion solution introduced through the upper inlet (in) of the infusion flow regulator is passed through the regulating flow path inlet 21a to enter the regulating flow path 21, and passed through the connecting flow path 22 and the collector flow path 23, and then the infusion solution is passed through the collector flow path outlet 23a to be finally discharged through the lower outlet (out).

At this time, when the rotary dial is turned, the position of the regulating flow path inlet 21a on the regulating flow path 21 is changed. That is, as shown in FIG. 7, after the infusion solution is injected into the regulating flow path 21 with the regulating flow path inlet 21a being positioned at a specific position of the regulating flow path 21, the infusion solution is moved along the recessed groove of the regulating flow path and enters the connecting flow path 22, and as the position of the regulating flow path inlet 21a on the regulating flow path 21 is changed by the rotation of the rotary dial, the length (s) and the width of the flow path change on the regulating flow path is changed, thereby regulating the flow rate.

In addition, in the present disclosure, the regulating flow path 21 is in the shape of a recessed groove with a certain width and height, which will be referred to as a first width and a first height, respectively, and the regulating flow path is divided into a first region (21-1 of FIG. 8) and a second region (21-2 of FIG. 8) based on the width and height. In the first region, the height is decreased but the width remains constant, and in the second region, both the width and the height are decreased. That is, in the present disclosure, the second region 21-2 of the regulating flow path is formed to decrease both in width and height. In addition, the collector flow path 33 is formed to be constant in width and height.

FIG. 8 shows the height and width of the regulating flow path 21 of the infusion flow regulator according to the present disclosure, in which the arc-shaped regulating flow path is straightened out to a linear form, and FIG. 8A shows the height of the regulating flow path, and FIG. 8B shows the width of the regulating flow path. As apparent from the drawings, the regulating flow path has the first region 21-1 in which the height is linearly decreased but the width remains constant, and the second region 21-2 in which both the width and height are decreased.

The division of the first region and the second region in the regulating flow path 21, that is, the position where the second region begins may be variously formed, and as an example, the second region may be formed over ⅓ to ½ of the entire length of the regulating flow path. Alternatively, the second region may begin at a point where the height of the regulating flow path, which is decreasing in the first region, becomes equal to the width. With this, the cross-section of the regulating flow path may have a rectangular shape in the first region, and the cross-section of the regulating flow path may have a square shape in the second region.

The regulating flow path formed according to the present disclosure is capable of regulating the flow rate accurately in a region where a very small flow rate flows, as shown in the experimental data below.

To this end, FIG. 9 is a conceptual view showing a flow of infusion solution flowing through the regulating flow path in the infusion flow regulator according to an embodiment of the present disclosure. Referring to FIGS. 7 and 9 together, the position of the regulating flow path inlet 21*a* may be changed on the regulating flow path 21 by rotating the rotary dial. FIGS. 7 and 9 show a situation when the regulating flow path inlet is located at a specific position on the regulating flow path, and for convenience of explanation, the situation when the regulating flow path inlet 21*a* is located in the connecting flow path 22 is referred to as an "angle 100%" and the situation when the regulating flow path inlet 21*a* is located at the other end of the regulating flow path is referred to as an "angle 0%", and the data comparing the effects of the related art and the present disclosure was calculated. That is, the greatest flow rate flows at a position of 100% angle.

Experiment was conducted, in which the second region was formed to begin at the point (30% angle point) where the height of the regulating flow path, which is decreasing in the first region, becomes equal to the width so that the cross-section of the regulating flow path in the second region is in a square shape, and the result of the experiment is shown in the experimental data shown below.

FIGS. 10 and 11 are graphs showing, by comparison, variations in height and width of the related infusion flow regulator and the infusion flow regulator according to the present disclosure. The solid line indicates data for the infusion flow regulator according to the present disclosure, and the dotted line indicates data for the related infusion flow regulator. Referring to the graph, it can be seen that the infusion flow regulator of the present disclosure maintains the cross-sectional area of the flow path in the micro flow rate region by less reduction in the height of the flow path, and reduction in the width of the flow path instead. That is, compared to the related technology in which the width remains constant while only the height is reduced in the micro flow rate region, the width is also reduced to keep the height at a relatively high level. Maintaining the cross-section as described above can provide advantages in processing because the small dimension portion is shortened.

FIG. 12 is a graph showing the enlarged micro flow rate region to show the flowing state of the flow rate of the related infusion flow regulator and the infusion flow regulator according to the present disclosure by comparison, and it can be seen that the related infusion flow regulator (dotted line) has a problem that the flow rate does not increase linearly at an angle 2% or less. This is because the aspect ratio between the width and height of the cross-section is too large, which makes the hydraulic area too small. The present disclosure solves this non-linear problem in the angle 0% region (micro flow rate region) in the related art, by having a linear graph shape even in the micro flow rate region as demonstrated by the result of the infusion flow regulator of the present disclosure (solid line).

FIG. 13 is a graph showing, by comparison, the hydraulic area in the microscopic flow rate range of the related infusion flow regulator and the infusion flow regulator according to the present disclosure. In the related art, it is shown that the hydraulic area is decreased in the micro flow rate region. This is because, as shown in FIG. 14, even with the same cross-sectional area, the flow paths have different flow resistances depending on whether the cross section is a square or a rectangle and thus have different areas hydro-dynamically. FIG. 14 shows, by comparison, the shape of the cross-section (a) of the regulating flow path in the micro flow rate region of the related infusion flow regulator, and the shape of the cross-section (b) of the regulating flow path in the micro flow rate region of the infusion flow regulator according to the present disclosure, thereby showing that the infusion flow regulator of the present disclosure maintains a larger hydraulic area compared to the related art even in the micro flow rate region.

What is claimed is:

1. An infusion flow regulator comprising:
   a main body including an inlet through which fluid is introduced and an outlet through which the fluid is discharged; and a rotary dial rotatably coupled to the main body, with a sealing member interposed therebetween, so as to regulate a flow rate of the fluid,
   wherein the rotary dial includes a regulating flow path shaped as a recessed groove having a first width and a first depth at a given cross section, and
   the regulating flow path includes:
      a first region in which the first width of the recessed groove remains constant in a first arcuate direction and the first depth of the recessed groove is decreased in the first arcuate direction, and
      a second region in which the first width of the recessed groove is decreased in the first arcuate direction and the first depth of the recessed groove is decreased in the first arcuate direction, and
   wherein the second region begins at a point where the first depth of the recessed groove becomes equal in value to the first width of the recessed groove.

2. The infusion flow regulator according to claim 1, further comprising a collector flow path shaped as a recessed groove and in communication with the regulating flow path to guide the fluid, wherein
   a width and a depth of the collector flow path are constant.

3. The infusion flow regulator according to claim 2, wherein the regulating flow path is an arc-shaped flow path, and the collector flow path is a circular flow path, wherein
   the infusion flow regulator further comprises a connecting flow path connecting the regulating flow path and the collector flow path.

4. The infusion flow regulator according to claim 1, wherein the first depth of the regulating flow path is linearly decreased in the first arcuate direction in the first region.

5. The infusion flow regulator according to claim 1, wherein the second region is formed over a region ⅓ to ½ of a length of the regulating flow path.

6. The infusion flow regulator according to claim 1, wherein a cross-section of the regulating flow path has a rectangular shape in the first region, and
a cross-section of the regulating flow path has a square shape in the second region.

7. An infusion flow regulator comprising:
a main body including an inlet through which fluid is introduced and an outlet through which the fluid is discharged; and a rotary dial rotatably coupled to the main body, with a sealing member interposed therebetween, so as to regulate a flow rate of the fluid,
wherein the rotary dial includes a regulating flow path shaped as a recessed groove having a first width and a first depth at a given cross section, and
the regulating flow path includes:
a first region in which the first width of the recessed groove remains constant in a first arcuate direction and the first depth of the recessed groove is decreased in the first arcuate direction, and
a second region in which the first width of the recessed groove is decreased in the first arcuate direction and the first depth of the recessed groove is decreased in the first arcuate direction.

8. The infusion flow regulator according to claim 7, further comprising a collector flow path shaped as a recessed groove and in communication with the regulating flow path to guide the fluid, wherein
a width and a depth of the collector flow path are constant.

9. The infusion flow regulator according to claim 8, wherein the regulating flow path is an arc-shaped flow path, and the collector flow path is a circular flow path, wherein
the infusion flow regulator further comprises a connecting flow path connecting the regulating flow path and the collector flow path.

10. The infusion flow regulator according to claim 7, wherein the first depth of the regulating flow path is linearly decreased in the first arcuate direction in the first region.

11. The infusion flow regulator according to claim 7, wherein the second region is formed over a region ⅓ to ½ of a length of the regulating flow path.

12. The infusion flow regulator according to claim 7, wherein a cross-section of the regulating flow path has a rectangular shape in the first region, and
a cross-section of the regulating flow path has a square shape in the second region.

* * * * *